(12) United States Patent
Matsunaga et al.

(10) Patent No.: US 7,294,761 B2
(45) Date of Patent: Nov. 13, 2007

(54) METHOD FOR EFFICIENTLY PRODUCING TRANSGENIC PLANT USING AUXIN PRECURSOR

(75) Inventors: Etsuko Matsunaga, Tokyo (JP); Koichi Sugita, Tokyo (JP); Hiroyasu Ebinuma, Tokyo (JP)

(73) Assignee: Nippon Paper Industries Co., Ltd., Tokyo (JP)

( * ) Notice: Subject to any disclaimer, the term of this patent is extended or adjusted under 35 U.S.C. 154(b) by 0 days.

(21) Appl. No.: 10/626,609

(22) Filed: Jul. 25, 2003

(65) Prior Publication Data

US 2004/0163143 A1 Aug. 19, 2004

(30) Foreign Application Priority Data

Jul. 26, 2002 (JP) ............................. 2002-218978

(51) Int. Cl.
| | |
|---|---|
| C12N 15/82 | (2006.01) |
| C12N 15/83 | (2006.01) |
| C12N 15/84 | (2006.01) |
| C12N 15/31 | (2006.01) |
| C12N 15/54 | (2006.01) |
| C12N 15/55 | (2006.01) |

(52) U.S. Cl. .................. 800/290; 800/282; 800/288; 800/294; 800/300; 800/323; 435/193; 435/195; 435/320.1; 435/456; 435/470

(58) Field of Classification Search ................ 800/278; 536/23.1; 435/320.1, 410
See application file for complete search history.

(56) References Cited

U.S. PATENT DOCUMENTS 5,965,791 A * 10/1999 Ebinuma et al. ............ 800/278

FOREIGN PATENT DOCUMENTS

| EP | 0 716 147 | 6/1996 |
|---|---|---|
| JP | 2000-83666 | 3/2000 |

OTHER PUBLICATIONS

Budar et al., 1986, Plant Science, vol. 46, pp. 195-206.*
Sitbon et al. Plant Physiology 99: 1062-1069 (1992).*
Spena et al. Molecular and General Genetics 227(2): 205-212 (Jun. 1991).*
Schmulling et al. The EMBO Journal 7(9): 2621-2629 (1988).*
Estruch et al. The EMBO Journal 10: 3125-3128 (1991).*
Woodward et al. Annals of Botany 95: 707-735 (2005).*
S. Endo, et al., Plant Cell Reports, vol. 20, No. 10, XP-002258506, pp. 923-928, "A New GST-MAT Vector Containing Both IPT and IAAM/H Genes can Produce Marker-Free Transgenic Tobacco Plants With High Frequency", Mar. 2002.
E. Prinsen, et al., Plant and Cell Physiology, vol. 31, No. 1, XP-009019606, pp. 69-75, "Functional Expression of Agrobacterium-Tumefaciens T-DNA ONC-Genes in Asparagus Crown Gall Tussues", 1990.
A. G. Depicker, et al., Plant Cell Reports, Springer-Verlag, vol. 7, XP-000564866, pp. 63-66, "A Negative Selection Scheme for Tobacco Protoplast-Derived Cells Expressing the T-DNA Gene 2", 1988.
G. A. Karlin-Neumann, et al., Plant Cell, vol. 3, No. 6, XP-000569698, pp. 573-582, "Phytochrome Control of the TMS2 Gene in Transgenic Arabidopsis: a Strategy for Selecting Mutants in the Signal Transduction Pathway", Jun. 1991.
J. Shah, et al., Molecular Plant-Microbe Interactions, vol. 10, No. 1, XP-000916767, pp. 69-78, "Characterization of a Salicylic Acid-Insensitive Mutant (sal1) of Arabidopsis Thaliana, Identified in a Selective Screen Utilizing the SA-Inducible Expression of the TMS2 Gene", 1997.

* cited by examiner

Primary Examiner—David T Fox
(74) Attorney, Agent, or Firm—Oblon, Spivak, McClelland, Maier & Neustadt, P.C.

(57) ABSTRACT

A method for producing a transgenic plant, which comprises: (A) introducing a vector into a plant cell, wherein the vector is a vector for gene introduction into a plant and comprises: a desired gene, and a selectable marker gene comprising a gene encoding an enzyme which synthesizes auxin from an auxin precursor; (B) culturing the plant cell into which the genes are introduced by the vector, in the presence of an auxin precursor and/or an analogue thereof to thereby prepare a redifferentiated tissue, and detecting and selecting the redifferentiated tissues; and (C) culturing the redifferentiated tissue selected in (B) to redifferentiate a plant individual, and a vector for gene introduction into a plant, which comprises: a desired gene, and a selectable marker gene comprising an indoleacetamide hydrolase, iaaH, gene and an isopentenyl transferase, ipt, gene and being free of an tryptophan monooxygenase, iaaM, gene.

13 Claims, 2 Drawing Sheets pIPT10

METHOD FOR EFFICIENTLY PRODUCING TRANSGENIC PLANT USING AUXIN PRECURSOR

BACKGROUND OF THE INVENTION

1. Field of the Invention

The present invention relates to a method for efficiently producing a transgenic plant using genetic engineering techniques, and a vector used for the method.

2. Brief Description of the Background Art

When a transgenic plant is produced by introducing a desired gene into a plant of interest, the following 3 steps are always required: (1) introduction of the desired gene into a plant cell, (2) selection of a plant tissue (desired gene-introduced tissue) containing desired gene-introduced cells, and (3) redifferentiation of a plant from the selected plant tissue. In the selection of a desired gene-introduced tissue among these steps, generally, it is not easy to select such tissue using expression of the desired gene alone as an index at the stage of cell culturing, so that the desired gene is introduced into a plant cell together with a selectable marker gene whose expression can be easily detected, and the desired gene-introduced tissue is selected based on the presence or absence of the expression of the selectable marker gene. The selectable marker gene used practically and frequently includes genes relating to drug resistances such as a kanamycin-resistant gene (NPTII: neomycin phosphotransferase gene) and a hygromycin-resistant gene (HPT: hygromycin phosphotransferase gene) which provide resistance to antibiotics, a sulfonylurea-resistant gene (ALS: acetolactate synthase gene) which provides resistance to agricultural chemicals, and the like.

When a gene relating to a drug resistance is used as the selectable marker gene, cells after gene introduction treatment are cultured using a medium containing such a drug, the presence or absence of the selectable marker gene, namely resistance to the drug, is evaluated, and selection is carried out using the evaluation as an index. Since such a drug originally has toxicity to plant cells, plant cells into which the selectable marker gene (so the desired gene) is not introduced die when cultured using such a medium. However, even if the resistance is present in this case, namely even if a plant cell can grow in the presence of such a drug, it is a matter of degree, so that bad influences of the culturing in the presence of such a drug upon plant cells cannot be avoided, thus actually causing problems such as reduction of a growth ratio and a redifferentiation ratio of desired gene-introduced tissue accompanied by the activity reduction of the plant cells.

In order to solve the problems, a novel vector for gene introduction into a plant and a gene introduction method into a plant using the vector have been proposed in JP-A-9-154580. When a gene is introduced using the vector and the method, desired gene-introduced tissue can be selected using only a morphological change in plant tissue after the gene introduction as an index, without using a drug which reduces the activity of plant cells.

In the above vector and method disclosed in JP-A-9-154580, a morphological abnormality induction gene such as a plant hormone synthetic gene is used as the selectable marker gene, and the desired gene-introduced tissue can be obtained as an adventitious bud or an adventitious root from a tissue after the gene introduction. However, among the adventitious buds and adventitious roots obtained in this manner, those to which the desired gene was not introduced (hereinafter also referred to as "escape") were present in a fairly large amount. It seems that a plant hormone and the like produced in a cell to which an morphological abnormality induction gene has been introduced together with the desired gene are transferred into its peripheral cells and have influence thereon, and tissue showing morphological abnormality is differentiated and proliferated also from the gene-unintroduced cells which has been influenced. It is generally considered to be difficult to introduce a gene into plants, and the adventitious bud originally has a poor redifferentiation ratio in the plants. Furthermore, selection efficiency of desired gene-introduced tissue is very poor due to the presence of this escape, so that improvements of the redifferentiation ratio and the selection efficiency have been particularly desired.

SUMMARY OF THE INVENTION

An object of the present invention is to provide a method for efficiently producing a transgenic plant, which can select desired gene-introduced tissue without using a drug which reduces the activity of plant cells and, what is more, with improved selection efficiency.

Another object of the present invention is to provide a vector used for the method.

These and other objects of the present invention have been accomplished by a method for producing a transgenic plant, which comprises:

(A) introducing a vector into a plant cell,
   wherein the vector is a vector for gene introduction into a plant and comprises:
   a desired gene, and
   a selectable marker gene comprising a gene encoding an enzyme which synthesizes auxin from an auxin precursor;
(B) culturing the plant cell into which the genes are introduced by the vector, in the presence of an auxin precursor and/or an analogue thereof to thereby prepare a redifferentiated tissue, and detecting and selecting the redifferentiated tissues; and
(C) culturing the redifferentiated tissue selected in (B) to redifferentiate a plant individual.

Also, these and other objects of the present invention have been accomplished by a vector for gene introduction into a plant, which comprises:
   a desired gene, and
   a selectable marker gene comprising an indoleacetamide hydrolase, iaaH, gene and an isopentenyl transferase, ipt, gene and being free of an tryptophan monooxygenase, iaaM, gene.

DETAILED DESCRIPTION OF THE INVENTION

Figure 1:
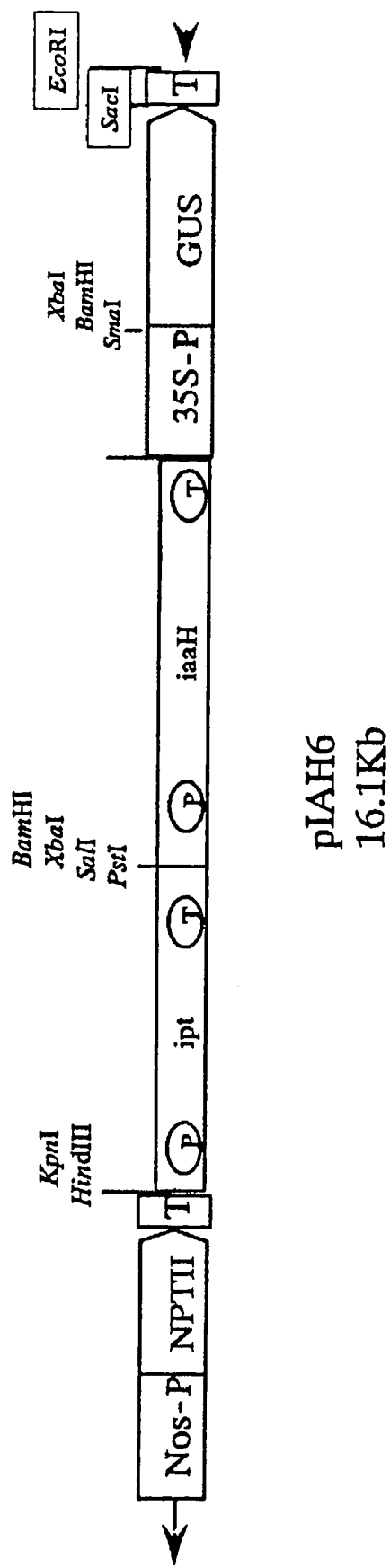
FIG. 1 is a schematic view showing a structure of T-DNA region to be integrated into a plant chromosome in a part of a pIAH6 vector.

As a result of intensive studies, the present inventors have accomplished the present invention by finding that the above objects can be achieved by artificially controlling the amount of auxin synthesized in desired gene-introduced cells.

In the method according to the present invention (hereinafter referred to as "method of the present invention"), an auxin precursor-auxin synthesis gene is used as a selectable marker gene. Auxin is a plant hormone and is known to accelerate elongation, proliferation and division of cells. For example, in the case of a plant pathogen *Agrobacterium tumefaciens* (hereinafter referred to as "*A. tumefaciens*"), tryptophan is converted into an auxin precursor indoleacetamide (IAM) through its oxidation by an enzyme tryptophan monooxygenase, and then IAM is hydrolyzed by an enzyme indoleacetamide hydrolase to thereby be converted into native auxin indoleacetic acid (IAA). In this case, the gene encoding a tryptophan monooxygenase is an iaaM gene, and the gene encoding an indoleacetamide hydrolase is an iaaH gene (D. Inze, M. Van Montagu, *Mol. Gen. Genet.*, 194: 265 (1984)). Auxin is not synthesized when the iaaH gene alone is present (Harry Klee, *Annu. Rev. Plant Physiol. Plant Mol. Biol.*, 42: 529-51 (1991)). Since analysis of the iaaH gene is fairly in progress as an auxin precursor-auxin synthesis gene, it can be easily obtained by those skilled in the art and therefore is preferable as a gene used in the present invention.

Also, in addition to the auxin precursor-auxin synthesis gene, other plant hormone synthesis genes such as the above iaaM gene and a cytokinin synthesis gene as a plant hormone which accelerates lateral bud proliferation and cell division can be used as the selectable marker gene. Particularly, when a cytokinin synthesis gene is used, it becomes possible to control production of a redifferentiated tissue from a plant cell into which a desired gene is introduced by the method of the present invention, by simply adjusting the concentration of an auxin precursor and/or an analogue thereof in the culturing medium. The most typical gene as the cytokinin synthesis gene is ipt gene (A.C. Smigocki, L. D. Owens, *Proc. Natl. Acad. Sci. USA*, 85: 5131 (1988)). Since analysis of this gene is also fairly in progress, it can be easily obtained by those skilled in the art and therefore is preferable as a gene used in the present invention.

According to the method of the present invention, the selectable marker gene comprising these plant hormone genes is inserted together with a desired gene into a vector known as a vector for gene introduction into a plant, and introduced into a plant cell. The vector can be introduced into a plant cell indirectly via a virus or bacterium which infects a plant or directly by physical and chemical techniques (I. Potrykus, *Annu. Rev. Plant Physiol. Plant Mol. Biol.*, 42: 205 (1991)).

When the vector is introduced via a virus or bacterium which infects a plant, for example, viruses such as cauliflower mosaic virus, Geminivirus, tobacco mosaic virus and brome mosaic virus and bacteria such as *A. tumefaciens* and *Agrobacterium rhizogenes* can be used. Furthermore, the method for introducing the vector by physical and chemical techniques includes a microinjection method, an electroporation method, a polyethylene glycol method, a fusion method, a high speed ballistic penetration method and the like.

The plant cell after the gene introduction is cultured in the presence of an auxin precursor and/or an analogue thereof to produce redifferentiated tissue such as an adventitious bud. In this case, the auxin precursor or an analogue thereof is a substance which is converted into auxin or a substance having a physiological activity similar to that of auxin (hereinafter also referred to as "auxin-like substance" as a whole) by the expression of the auxin precursor-auxin synthesis gene introduced as a selectable marker gene. For example, when the above iaaH gene is expressed, indoleacetamide hydrolase is synthesized, and in addition to its original substrate IAM, this enzyme also hydrolyzes naphthaleneacetic acid amide (NAM) to convert it into a synthetic auxin naphthaleneacetic acid (NAA). Accordingly, when the iaaH gene is used as the auxin precursor-auxin synthesis gene in the present invention, NAM can also be used as an analogue of an auxin precursor similar to the case of an auxin precursor IAM.

Also, it is known that production of redifferentiated tissue such as an adventitious bud is mainly controlled by cytokinin and auxin. That is, when the cytokinin/auxin ratio is high, differentiation of buds is induced, and when the cytokinin/auxin ratio is low, differentiation of roots is induced (John D. HaMill, *Aust. J. Plant Physiol.*, 20: 405 (1993)).

On the other hand, an auxin precursor-auxin synthesis gene is also introduced as a selectable marker gene into the desired gene-introduced cell of the present invention. Thus, redifferentiated tissue such as a desired gene-introduced adventitious bud can be produced by culturing the gene-introduced plant cell using a medium supplemented with appropriate amounts of an auxin precursor and/or an analogue thereof (hereinafter also referred to as "auxin precursor, etc.") and cytokinin. Since the auxin precursor, etc. are converted into auxin-like substances in the desired gene-introduced pant cell by the action of an auxin precursor-auxin synthesis gene in response to its added amount, appropriate amounts of auxin and cytokinin are eventually provided in the desired gene-introduced pant cell when cultured using a medium supplemented with appropriate amounts of the auxin precursor, etc. and cytokinin, so that they have a cytokinin/auxin ratio optimum for the redifferentiation of adventitious buds and the like. On the other hand, a cell into which the desired gene is not introduced takes actions different from the desired gene-introduced cell. That is, since the auxin precursor-auxin synthesis gene is not introduced into the cell, it has extremely low ability to use the auxin precursor, etc. as auxin so that it can use mainly cytokinin alone among the auxin precursor, etc. and cytokinin added to the medium.

Furthermore, when a cytokinin synthesis gene is used as the selectable marker gene of the present invention together with an auxin precursor-auxin synthesis gene, as described above, a desired gene-introduced adventitious bud and the like can be redifferentiated by simply culturing the gene introduction-treated plant cell using a medium in which the concentration of an auxin precursor and/or an analogue thereof is appropriately set. That is, in the desired gene-introduced cell in this case, the auxin precursor, etc. are converted into auxin-like substances in response to the added amount, and cytokinin is actively synthesized by the cytokinin synthesis gene without adding cytokinin to the medium, so that the cytokinin/auxin ratio in the desired gene-introduced cell becomes a value optimum for the redifferentiation of adventitious bud and the like when the cell is cultured using a medium to which appropriate amounts of the auxin precursor, etc. are added. On the other hand, a cell into which the desired gene is not introduced takes actions significantly different from the desired gene-introduced cell. That is, since the auxin precursor-auxin synthesis gene and the cytokinin synthesis gene are not introduced into this cell, such plant hormones are hardly produced.

As is apparent from the above, according to the method of the present invention, the frequency of escape can be reduced by preferentially redifferentiating the desired gene-introduced adventitious bud and the like by controlling amounts of the auxin precursor and/or an analogue thereof and cytokinin to be added to the medium. Particularly, larger effects can be obtained when a cytokinin synthesis gene is used together with an auxin precursor-auxin synthesis gene as the selectable marker gene.

Specific amounts of the auxin precursor, etc. and cytokinin to be added practically to the medium can be optionally determined depending on the kinds of these plant hormones and the kinds of the plant from which a transformant is produced by the method of the present invention. In determining the amounts, for example, a gene introduction treatment is applied to a plant from which a transformant is produced, using a vector containing a selectable marker gene used in the present invention and a reporter gene such as GUS (β-D-glucuronidase) gene. By culturing the tissue after the gene introduction by changing kinds and amounts of the auxin precursor, etc. and cytokinin in the medium in several steps, an adventitious bud and the like are redifferentiated to examine expression of the reporter gene. Since conditions under which a redifferentiation ratio of the reporter gene-expressing adventitious bud and the like becomes highest in this case are conditions most suitable for the production of redifferentiated tissue of the desired gene-introduced plant cell, so that such conditions may be employed regarding the kinds and amounts of the auxin precursor, etc. and cytokinin in producing a transformant by introducing the desired gene into the plant by the method of the present invention.

Also, other components necessary for the proliferation and differentiation of plant cells and/or other components not necessary for the proliferation and differentiation of plant cells, in addition to the auxin precursor, etc. and cytokinin, can be added to the above medium for the production of redifferentiated tissues, within such a range that they do not spoil the object of the present invention. The medium includes a solid medium prepared by adding the auxin precursor, etc. and cytokinin, 1 to 3 w/v % of sucrose as the carbon source and 0.5 to 1.0 w/v % of agar or 0.1 to 0.4 w/v % of gellan gum as a solidifying agent to a basal medium per se such as MS (Murashige and Skoog, *Physiol. Plant*, 15: 473-497 (1962)) or WPM (Loyd and McCown, *Prop. Int. Plant Prop. Soc.*, 30: 421-427 (1980)) or to such a basal medium slightly modified to suit for the plant for the production of a transformant.

According to the method of the present invention, the thus obtained redifferentiated tissue such as an adventitious bud is detected and selected and a plant individual is redifferentiated to thereby produce a transgenic plant into which a desired gene is introduced. Since the tissue to be selected is redifferentiated tissue such as an adventitious bud, it can be detected and selected with the naked eye without using special reagents and tools. In addition, due to synergetic action of the auxin precursor-auxin synthesis gene introduced as a selectable marker gene and the auxin precursor and/or an analogue thereof added to the medium to be used for the redifferentiated tissue production, frequency of the desired gene-introduced into the redifferentiated tissue selected in this manner is higher than that in the conventional case. Accordingly, since the selection efficiency of a desired gene-introduced tissue is excellent, a transgenic plant into which the desired gene is introduced can be efficiently produced by redifferentiating the thus obtained redifferentiated tissue into a plant individual.

For example, when the thus obtained redifferentiated tissue is an adventitious bud, its redifferentiation into a plant individual can be carried out by cutting out the adventitious bud as such or after growing it to a degree and then planting it on a rooting medium for rooting. In this case, it is preferable that the culturing temperature is from 15 to 30° C. and the light intensity is less than 50 µmol/m$^2$/s. The rooting medium includes a liquid medium prepared by adding one or more of auxins such as NAA and indolebutyric acid as plant hormones to the above basal medium or a dilution thereof and further supplementing with 5 to 30 g/l sucrose as the carbon source, or a solid medium prepared by solidifying it with agar or the like.

Moreover, the vector according to the present invention (hereinafter referred to as "vector of the present invention") is a vector for gene introduction into a plant, which comprises a desired gene and as selectable marker gene comprising an iaaH gene and an ipt gene and being free of an iaaM gene in the gene introduction region into plant chromosome. The method of the present invention can achieve its object at a higher level by carrying it using a vector of such a construction.

A vector used in the method of the present invention and the above vector of the present invention may contain other genes and factors (DNA sequences having specific functions) in addition to the genes so far described, within such a range that they do not spoil the object of the present invention. For example, as proposed in JP-A-9-154580, when an auxin precursor-auxin synthesis gene and a cytokinin synthesis gene are used in combination with a removable DNA element, the genes used as the selectable marker gene can be removed after selection of redifferentiated tissues, so that it becomes possible to obtain a transgenic plant from which influences of the selectable marker gene are completely excluded. The removable DNA element can be obtained from a transposon or a site-specific recombination system.

Kinds of the plant to which the method and vector of the present invention can be applied are not particularly limited. However, the method and vector of the present invention can have particularly great effects when applied to plants considered to be difficult in producing transformants such as woody plants.

In addition, kinds of the desired genes to be introduced into plants using the method and vector of the present invention are not limited, too. They can be freely selected in response to each object, such as a gene which can provide agriculturally superior character and a gene which cannot always provide agriculturally superior character but is necessary for studying gene expression mechanism.

In the plant tissue culturing, plant hormones auxin and cytokinin are deeply concerned in each step of the method for redifferentiating a plant individual from cultured tissue. This is not an exception regarding the production of redifferentiated tissue such as an adventitious bud, too. As described above, production of an adventitious bud and the like is controlled by the cytokinin/auxin ratio, and a cell produces an adventitious bud or the like for the first time when the cytokinin/auxin ratio in the cell becomes an appropriate value.

Consequently, the frequency of obtaining a desired gene-introduced redifferentiated tissue is low when the desired gene is introduced into a plant cell merely using a cytokinin synthesis gene and/or an auxin synthesis gene as a selectable marker gene. In this case, cytokinin and auxin are actively produced in the desired gene-introduced cell by the action of the selectable marker gene, but the productivity cannot be controlled artificially so that the cytokinin/auxin ratio in the plant hormone genes-introduced cell, namely the desired gene-introduced cell, does not always become an appropriate value. Accordingly, the cells do not always preferentially redifferentiate cells into which the desired gene is not introduced.

Thus, according to the present invention, an auxin precursor-auxin synthesis gene is used as a selectable marker gene, and the amount of auxin synthesized in the desired gene-introduced cell is artificially controlled by its synergetic action with the auxin precursor, etc. That is, gene introduction is applied to plant tissue using an auxin precursor-auxin synthesis gene as a selectable marker gene together with a desired gene, and the plant tissue is cultured using a medium supplemented with an auxin precursor and/or an analogue thereof As a result, auxin is produced in the desired gene-introduced cell in response to the concentration of the auxin precursor, etc. in the medium, so that the amount of auxin in the cell can also be controlled by controlling the amount of the auxin precursor, etc. to be added to the medium. In this case, when a predetermined amount of cytokinin as the other plant hormone is supplied into a desired gene-introduced cell by adding it to the medium together with an auxin precursor or the like or by introducing a cytokinin synthesis gene into the cell together with an auxin precursor-auxin synthesis gene, the cytokinin/auxin ratio in the cell is also controlled as a result.

According to the present invention, the cytokinin/auxin ratio in the desired gene-introduced cell is controlled at a level optimum for the redifferentiation of an adventitious bud and the like to thereby accelerate the production of redifferentiated tissue from the cell, and a desired gene-introduced adventitious bud or the like is preferentially redifferentiated from the plant tissue after the gene introduction to thereby reduce the frequency of escape. It is considered that the effect is particularly large when a cytokinin synthesis gene is used together with an auxin precursor-auxin synthesis gene as the selectable marker gene. In this case, there is a large difference in the intracellular physiological environment regarding plant hormones between the desired gene-introduced cell and the cell into which it is not introduced, in comparison with a case in which an auxin precursor-auxin synthesis gene alone is used as the selectable marker gene. Therefore, it is considered that the desired gene-introduced cell shows more preferential adventitious bud-differentiating ability when it is cultured by adding an appropriate amount of the auxin precursor, etc. to the medium.

According to the present invention, the cytokinin/auxin ratio in a desired gene-introduced plant cell can be controlled artificially. Consequently, the cytokinin/auxin ratio in a desired gene-introduced cell can be controlled at a level most suitable for the production of redifferentiated tissue such as an adventitious bud, redifferentiation of the cell can be accelerated and an adventitious bud and the like can be preferentially redifferentiated from the cell.

Thus, the present invention reduces frequency of so-called escape and thereby improves selection efficiency of desired gene-introduced tissue and improves the obtaining ratio of a transformant. Such effects are particularly large when applied to a plant considered to be difficult for producing a transformant. Therefore, according to the present invention, a transgenic plant can be produced efficiently.

In addition, according to the present invention, as a result that a selectable marker gene is used in combination with a removable DNA element, it becomes possible to produce a transgenic plant from which influence of the used selectable marker gene is completely excluded.

That is, even in a plant from which a transformant cannot be produced easily, a transformant can be efficiently produced and, what is more, a transgenic plant from which influence of selectable marker gene is completely excluded and into which a desired gene alone is introduced can be produced according to the present invention.

The present invention is described below based on Examples; however, the present invention is not limited thereto.

EXAMPLE 1

Using a plasmid pIAH6 as a vector having a GUS gene as a model of a desired gene and an ipt gene and an iaaH gene as selectable marker genes, a transformant was produced by carrying out gene introduction into *Eucalyptus globulus* (hereinafter referred to as "*E. globulus*") by the method of the present invention.

In the structure of pIAH6, a region to be integrated into a plant chromosome (T-DNA region) is shown in FIG. 1. In the drawing, circled P and T indicate the promoter and polyadenylation signal of the ipt gene and the iaaH gene, respectively, NOS-P indicates the promoter of nopaline synthase gene, T indicates the polyadenylation signal of nopaline synthase gene, and 35S-P indicates the 35S promoter of cauliflower mosaic virus. Also, the black arrowheads on both termini of the drawing indicate RB site and LB site which divide the T-DNA region. Other moieties than the T-DNA region of this plasmid have the same structures of the corresponding moieties of a commercially available plant gene introduction vector pBI121 (manufactured by TOYOBO).

This plasmid pIAH6 has been introduced into *Escherichia coli* JM109, and the *E coli* has been deposited as *E. coli* JM109 (pIAH6) on Jul. 16, 2003, as FERM BP-8429 in International Patent Organism Depositary, National Institute of Advanced Industrial Science and Technology (AIST Tsukuba Central 6, 1-1, Higashi 1-Chome Tsukuba-shi, Ibaraki-ken, Japan).

I. Introduction of Plasmid pIAH6 into *Agrobacterium*

*A. tumefaciens* EHA105 was inoculated into 10 ml of YEB liquid medium (5 g/l beef extract, 1 g/l yeast extract, 1 g/l peptone, 5 g/l sucrose, 2 mM $MgSO_4$, pH 7.2 at 22° C. (hereinafter, pH at 22° C., unless otherwise indicated)) and cultured at 28° C. until OD630 reached a range of from 0.4 to 0.6. The culture broth was centrifuged at 6,900×g and at 4° C. for 10 minutes to collect cells, the thus collected cells were suspended in 20 ml of 10 mM HEPES (pH 8.0) and again centrifuged at 6,900×g and at 4° C. for 10 minutes to collect cells, and then the thus collected cells were suspended in 200 μl of the YEB liquid medium and used as a cell suspension for plasmid introduction.

The plasmid pIAH6 was introduced into cells of *Agrobacterium* by mixing 50 μl of the thus prepared cell suspension for plasmid introduction with 3 μl of the above pIAH6 in a 0.5 ml capacity tube (manufactured by Assist), followed by electroporation (Gene Pulser II System (manufactured by BIORAD)). After the electroporation, 200 μl of YEB liquid medium was added to the mixture, followed by culturing at 25° C. for 1 hour on a shaker, and the thus obtained cells were inoculated onto a YEB agar medium (1.5 w/v % agar, other components are as described below) supplemented with 50 mg/l kanamycin and cultured at 28° C. for 2 days to for cell colonies of *A. tumefaciens*. Introduction of pIAH6 into *A. tumefaciens* EHA105 was confirmed by extracting the plasmid from the cells of the colony by the alkali method, digesting the plasmid with restriction enzymes HindIII, SmaI and EcoRI and then analyzing the digest by agarose gel electrophoresis.

II. Introduction of pIAH6 into Eucalyptus

Seeds of *E. globulus* from Chile were sterilized by soaking in 70% ethanol for about 1 minute and then soaking with stirring in a 2% aqueous sodium hypochlorite solution for about 4 hours, washed thoroughly with sterile water, inoculated on an MS agar medium to which 0.5 mg/l zeatin had been added and stored in a refrigerator at 4° C. for 2 days to accelerate germination, and then the germination was carried out by culturing at 25° C. under light conditions of about 10 μmol/m$^2$/s in light intensity. One to two weeks after the inoculation of the seeds onto the germination medium, hypocotyls were collected by cutting out apical buds, cotyledons and roots of the germinated seedlings, and the hypocotyls were cut into sections of about 5 mm to be used as samples for gene introduction and subjected to the following test.

*A. tumefaciens* EHA105 introduced with the plasmid pIAH6 in the above item I was cultured overnight in the YEB liquid medium and then diluted to $OD_{630}$ =0.5 with EG basal medium, and the sections of hypocotyl prepared in the above were soaked in the cell suspension. Next, each of the sections after removing excess cell suspension was co-cultured with *Agrobacterium* on an agar medium (agar 8.5 g/l) prepared by adding 1.0 mg/l zeatin, 0.05 mg/l NAA and 40 mg/l acetosyringone to the EG basal medium, at 25° C. for 3 days in the dark to thereby infect each section with the pIAH6-introduced *Agrobacterium*. In this case, a modified MS medium having an ammonia nitrogen/nitrate nitrogen concentration ratio of 1:3 (5 mM $NH_4$, 15 mM $NO_3$) was supplemented with 20 g/l sucrose and used as the EG basal medium.

The sections after infection culturing were put on an EG basal agar medium (agar 8.5 g/l) supplemented with 500 mg/l ticarcillin and 1 μM or 10 μM of an auxin precursor analogue NAM, and the culturing was continued at 25° C. under light conditions of 30 to 40 μmol/m$^2$/s in light intensity while sub-culturing at an interval of 2 weeks using the same medium. Among these sections, the quicker ones redifferentiated adventitious buds after about 2 months of the *Agrobacterium* infection.

Three months after the *Agrobacterium* infection, in order to examine expression of the GUS gene used as a model of the desired gene, the redifferentiated adventitious buds were subjected to a GUS staining test in accordance with the method of Jefferson et al. (*Plant Mol. Biol. Rep.*, 5: 387-405 (1987)), and the degree of formation of desired gene-introduced adventitious buds was judged by examining the number of stained adventitious buds (the number of adventitious buds expressing the desired gene). The results are shown in Table 1.

TABLE 1

Effects of iaaH gene and addition of NAM in the production of transformant of *E. globulus*

| NAM conc. (μM) | A Tested sample (number of sections) | B Adventitious bud differentiated *1 (number of sections) | B/A Redifferentiation ratio (%) | C GUS + adventitious bud differentiated *2 (number of sections) | C/B Selection efficiency (%) | C/A Gene introduction ratio (%) |
|---|---|---|---|---|---|---|
| 1 | 60 | 21 | 35.0 | 8 | 38.1 | 13.3 |
| 10 | 48 | 2 | 4.2 | 1 | 50.0 | 2.1 |

*1 The number of sections which differentiated an adventitious bud
*2 The number of sections which differentiated a GUS-stained adventitious bud As is apparent from Table 1, when the redifferentiation ratio of adventitious buds, the selection efficiency (frequency of the introduction of the desired gene into the redifferentiated adventitious bud) and the gene introduction ratio (ratio of obtaining desired gene-introduced adventitious bud) were calculated based on the sections as the sample for gene introduction, they were 35.0%, 38.1% and 13.3%, respectively, at a NAM concentration of 1 μM, and were 4.2%, 50.0% and 2.1%, respectively, at a NAM concentration of 10 μM.

Comparative Example 1

An *E. globulus* gene introduction test was carried out in the same manner as in Example 1, except that the hypocotyl sections after the *Agrobacterium* infection were cultured using the EG basal agar medium (agar 8.5 g/l) supplemented with 500 mg/l ticarcillin and 0 μM, 1 μM or 10 μM NAA as auxin. The results are shown in Table 2.

TABLE 2

Effect of iaaH gene and addition of NAA in the
production of transformant of *E. globulus*

| NAM conc. (μM) | A Tested sample (number of sections) | B Adventitious bud differentiated *1 (number of sections) | B/A Redifferentiation ratio (%) | C GUS + adventitious bud differentiated *2 (number of sections) | C/B Selection efficiency (%) | C/A Gene introduction ratio (%) |
|---|---|---|---|---|---|---|
| 0 | 58 | 6 | 10.3 | 0 | 0 | 0 |
| 1 | 62 | 9 | 14.5 | 2 | 22.2 | 3.2 |
| 10 | 40 | 13 | 32.5 | 1 | 7.7 | 2.5 |

*1 The number of sections which differentiated an adventitious bud
*2 The number of sections which differentiated a GUS-stained adventitious bud As is apparent from Table 2, the selection efficiency was low in all cases, and it reached only 22.2% on the section basis even in the case of the addition of 1 μM NAA which showed the highest value.

Comparative Example 2

An *E. globulus* gene introduction test was carried out in the same manner as in Example 1 or Comparative Example 1, except that a plasmid pIPT10 having only the ipt gene as the selectable marker gene was used as the vector. Also, the vector also has the GUS gene as a model of the desired gene.

Figure 2:
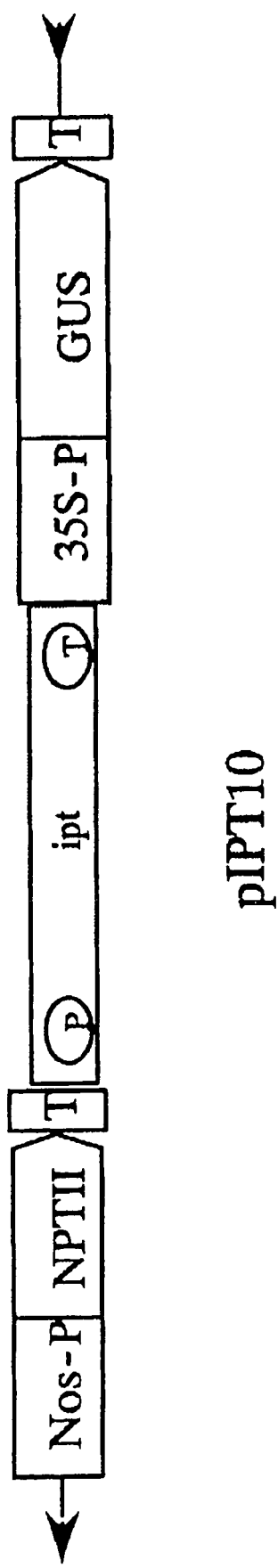
FIG. 2 is a schematic view showing a structure of T-DNA region to be integrated into a plant chromosome in a part of a pIPT 10 vector.

Structure of T-DNA region of the pIPT10 used in this case is shown in FIG. 2, and results of the gene introduction test are shown in Table 3.

TABLE 3

Effect of ipt gene in the production of transformant of *E. globulus*

| Conc. of additives (μM) | | A Tested sample (number of sections) | B Adventitious bud differentiated *1 (number of sections) | B/A Redifferentiation ratio (%) | C GUS + adventitious bud differentiated *2 (number of sections) | C/B Selection efficiency (%) | C/A Gene introduction ratio (%) |
|---|---|---|---|---|---|---|---|
| — | 0 | 46 | 3 | 6.5 | 0 | 0 | 0.0 |
| NAM | 1 | 46 | 2 | 4.4 | 0 | 0 | 0.0 |
| | 10 | 46 | 0 | 0 | 0 | 0 | 0.0 |
| NAA | 1 | 44 | 9 | 20.5 | 1 | 11.1 | 2.3 |
| | 10 | 44 | 7 | 15.9 | 0 | 0 | 0.0 |

*1 The number of sections which differentiated an adventitious bud
*2 The number of sections which differentiated a GUS-stained adventitious bud As is apparent from Table 3, the selection efficiency was also low in this case, and it reached only 11.1% on the section basis even in the case of the addition of 1 μM NAA which showed the highest value.

EXAMPLE 2

A transformant was produced by carrying out gene introduction into a populus hybrid (*Populus sieboldii×Populus grandidentata*) by the method of the present invention using the pIAH6 used in Example 1 as the vector.

A stem of an aseptic seedling of a populus hybrid strain Y63 (collected from the experimental forests belonging to Akita Jujo Kasei) was cut into a section of 5 mm in length such that it did not contain a node, and this was further cut into two in lengthwise and infected with pIAH6-introduced *A. tumefaciens* LBA4404 (purchased from CLONTECH) to thereby introduce pIAH6 into the populus hybrid strain Y63. That is, the pIAH6-introduced *A. tumefaciens* LBA4404 obtained in the same manner as in Example 1 was cultured overnight in the YEB liquid medium and then diluted to $OD_{630}=0.5$ with Y basal medium, and the stem sections prepared in the above were soaked in this cell suspension. Next, each of these sections after removing excess cell suspension was co-cultured with *Agrobacterium* on an agar medium (agar 8 g/l) prepared by adding 40 mg/l acetosyringone to the Y basal medium, at 25° C. for 3 days in the dark to thereby be infect with the pIAH6-introduced *Agrobacterium*. In this case, a modified MS medium (10 mM $NH_4$, 30 mM $NO_3$) was supplemented with 20 g/l sucrose and used as the Y basal medium.

The sections after infection culturing were put on the Y basal agar medium (agar 8 g/l) supplemented with 500 mg/l ticarcillin and 1 μM, 5 μM or 30 μM of an auxin precursor analogue NAM, followed by culturing at 25° C. under light conditions of 30 to 40 μmol/m²/s in light intensity. Two months thereafter, a redifferentiated adventitious bud was selected and separated, culturing of this adventitious bud was continued under the same conditions, and then 2 months thereafter (4 months after commencement of the culturing in the presence of NAM), morphology of the cultured tissue was observed to judge if the desired gene is introduced into the selected adventitious bud. In this case, when the desired gene is introduced into the selected adventitious bud, the cultured tissue shows a multiple bud form by the action of the simultaneously introduced selectable marker gene (ipt gene), but when the desired gene is not introduced, namely when the selected adventitious bud is an escape, the cultured tissue does not show a multiple bud form. That is, since the ipt gene is not introduced into the escape, the adventitious bud was redifferentiated by mere influence of a desired gene-introduced cell which was present adjacent thereto.

The results are shown in Table 4.

TABLE 4

Effect of iaaH gene and addition of NAM in the production of transformant of populus hybrid

| NAM conc. (μM) | A Tested sample (number of sections) | B Adventitious bud differentiated *1 (number of sections) | B/A Redifferentiation ratio (%) | C GUS + adventitious bud differentiated *2 (number of sections) | C/B Selection efficiency (%) | C/A Gene introduction ratio (%) |
|---|---|---|---|---|---|---|
| 0 | 10 | 0 | 0 | 0 | 0 | 0 |
| 1 | 10 | 7 | 70.0 | 5 | 71.4 | 50.0 |
| 5 | 10 | 6 | 60.0 | 4 | 66.7 | 40.0 |
| 30 | 10 | 0 | 0 | 0 | 0 | 0 |

*1 The number of sections which differentiated an adventitious bud
*2 The number of sections which differentiated an adventitious bud judged as a multiple bud by observation after culturing for 4 months As is apparent from Table 4, desired gene-introduced adventitious buds were obtained in the case of the NAM concentration of 1 μM and 5 μM, and the selection efficiency when calculated on the section basis was 50.0% in the case of the NAM concentration of 1 μM and 40.0% in the case of the NAM concentration of 5 μM. In this connection, tough not shown in the table, the total number of adventitious buds redifferentiated at an NAM concentration of 1 μM was 67, and the desired gene was introduced into 6 of them. Also, a total of 34 adventitious buds were redifferentiated at an NAM concentration of 5 μM, and the desired gene was introduced into 5 of them.

Comparative Example 3

A gene introduction test on the populus hybrid was carried out in the same manner as in Example 2, except that the stem sections after *Agrobacterium* infection were cultured using the Y basal agar medium (agar 8 g/l) supplemented only with 500 mg/l ticarcillin. The results are shown in Table 4.

As shown in Table 4, adventitious buds were not redifferentiated in this case, and redifferentiated individuals into which the desired gene was introduced were also not obtained.

EXAMPLE 3

Definite buds of a high rooting clone of *E. globulus* from Chile were aseptically grown using a medium prepared by adding 0.5 mg/l zeatin to the Y basal medium of Example 2, and the elongated stems were cut into sections of 5 mm to be used as samples for gene introduction and infected with the plasmid pIAH6-introduced *Agrobacterium* in the same manner as in Example 1.

The sections after infection culturing were put on an EG basal agar medium (agar 8.5 g/l) supplemented with 500 mg/l ticarcillin and 1 μM of an auxin precursor analogue NAM, and the culturing was continued at 25° C. under light conditions of 30 to 40 μmol/m²/s in light intensity while sub-culturing at an interval of 2 weeks using the same medium.

Four months after the *Agrobacterium* infection, the redifferentiated adventitious buds were subjected to a GUS staining test in accordance with the above method of Jefferson et al., and the degree of formation of desired gene-introduced adventitious buds was judged.

As a result, adventitious buds were differentiated from 5 sections among 40 of the stem sections, and it was confirmed that the desired gene was introduced into the buds derived from 3 sections among them. That is, the redifferentiation ratio of adventitious buds, the selection efficiency and the gene introduction ratio into adventitious buds were 12.5%, 60.0% and 7.5%, respectively, based on the sections as the sample for gene introduction. When cloned seedlings of *E. globulus* are used as the material for gene introduction, it is a surprising fact that a gene-introduced adventitious bud was obtained at a frequency of 7.5% based on the gene-introduced samples.

Comparative Example 4

Using plasmid pIPT10 as the vector, a gene introduction test was carried out into a high rooting clone of *E. globulus* in the same manner as in Example 3. However, adventitious buds were not redifferentiated in this case, and redifferentiated individuals into which the desired gene was introduced were also not obtained.

While the invention has been described in detail and with reference to specific embodiments thereof, it will be apparent to one of skill in the art that various changes and modifications can be made therein without departing from the spirit and scope thereof All references cited herein are incorporated in their entirety.

This application is based on Japanese application No. 2002-218978 filed on Jul. 26, 2002, the entire contents of which are incorporated hereinto by reference.

What is claimed is:

1. A method for producing a transgenic plant, comprises:
  (A) transforming a plant cell with a gene introduction vector which comprises a desired polynucleotide sequence,
   a selectable marker polynucleotide comprising an *iaaH* gene which encodes indoleacetamide hydrolase,
   an *ipt* gene encoding isopentenyl transferase;
  (B) culturing the transformed plant cell described in (A) in a medium containing indoleacetamide or naphthaleneacetamide that is hydrolyzed into the auxin indoleacetc acid (IAA) or the auxin analog napthaleneacetic acid (NAA) by indoleacetamide hydrolase under conditions suitable for production of a redifferentiated plant tissue expressing said desired polynucleotide sequence and said selectable marker polynucleotide from said transformed plant cell, (C) detecting and selecting the redifferentiated plant tissue described in (B), and (D) culturing the redifferentiated tissue described in (C) into a transgenic plant comprising said desired polynucleotide sequence.

2. The method of claim 1, wherein said selectable marker polynucleotide synthesizes the auxin indoleacetic acid (IAA).

3. The method of claim 1, wherein said selectable marker polynucleotide synthesizes the auxin naphthaleneacetic acid (NAA).

4. The method of claim 1, wherein the vector is introduced via a plant virus.

5. The method of claim 1, wherein the vector is introduced using *Agrobacterium*.

6. The method of claim 1, wherein the vector is introduced by a physical or chemical technique.

7. The method of claim 1, wherein the vector comprises a GUS gene.

8. The method of claim 1, wherein the vector comprises a kanamycin resistance gene.

9. The method of claim 1, wherein the vector comprises a hygromycin resistance gene.

10. The method of claim 1, wherein the vector comprises a sulfonylurea resistance gene.

11. The method of claim 1, wherein the plant cell is *Eucalyptus*.

12. The method of claim 1, wherein the plant cell is *Populus*.

13. A vector for introducing a desired polynucleotide into a plant comprising:

a desired polynucleotide, and a selectable marker gene comprising an indoleacetamide hydrolase, iaaH, gene and an isopenteny transferase, ipt, gene, wherein said vector is free of the tryptophan monooxygenase, iaaM, gene.

* * * * *